(12) United States Patent
Jones et al.

(10) Patent No.: US 6,479,060 B1
(45) Date of Patent: Nov. 12, 2002

(54) ELEGANT HYDROGENATED CASTOR OIL OINTMENTS

(75) Inventors: David P. Jones, San Antonio, TX (US); David W. Hobson, San Antonio, TX (US); Pilar P. Duque, San Antonio, TX (US)

(73) Assignee: Healthpoint, Ltd., Fort Worth, TX (US)

( * ) Notice: Subject to any disclaimer, the term of this patent is extended or adjusted under 35 U.S.C. 154(b) by 0 days.

(21) Appl. No.: 09/945,903

(22) Filed: Sep. 4, 2001

(51) Int. Cl.⁷ ............. A61K 7/48; A61K 7/32; A61K 7/42; A61F 13/00
(52) U.S. Cl. ............. 424/401; 424/49; 424/59; 424/62; 424/401; 424/405; 424/443; 514/96.9; 514/887; 514/944
(58) Field of Search ............. 424/195.1, 401; 514/331, 887, 96.9, 944

(56) References Cited

U.S. PATENT DOCUMENTS

| | | | |
|---|---|---|---|
| 4,293,565 A | | 10/1981 | Cordes |
| 4,349,563 A | | 9/1982 | Gilbert |
| 4,803,067 A | | 2/1989 | Brunetta |
| 4,853,222 A | * | 8/1989 | Avelle et al. ............ 424/195.1 |
| 5,021,429 A | * | 6/1991 | Martin-Smith et al. ..... 514/331 |
| 5,102,656 A | | 4/1992 | Kasat |
| 5,362,497 A | | 11/1994 | Yamada |
| 5,728,391 A | | 3/1998 | Ikeya |
| 5,759,997 A | | 6/1998 | Cavanak |
| 5,837,735 A | | 11/1998 | Miyata et al. |
| 5,869,088 A | | 2/1999 | Hosokawa |
| 6,063,762 A | | 5/2000 | Hong |
| 6,068,855 A | | 5/2000 | Leslie |
| 6,096,338 A | | 8/2000 | Lacy |

* cited by examiner

Primary Examiner—Thurman K. Page
Assistant Examiner—Micah-Paul Young
(74) Attorney, Agent, or Firm—McKee, Voorhees & Sease, P.L.C.

(57) ABSTRACT

A topical ointment pharmaceutical composition that uses a lipophilic base, a pharmaceutical active and, dispersed in the base, from about 1% to about 50% by weight of the total composition of hydrogenated non-melted castor oil in powder form. The result of using hydrogenated non-melted castor oil in powder form is a surprising pharmaceutical elegance perceived to be smoother in texture and more spreadable than an ointment made by melting the hydrogenated castor oil.

6 Claims, No Drawings

ELEGANT HYDROGENATED CASTOR OIL OINTMENTS

FIELD OF THE INVENTION

This invention relates to topical pharmaceutical compositions.

BACKGROUND OF THE INVENTION

Topical pharmaceutical compositions are, of course, well known. They can be used as water proofing agents, sunscreens, skin conditioning agents, lip balms, wound dressings, hair pomades, etc. Regardless of the specific use, common to pharmaceutically satisfactory topical actives are that they must stay on the skin for a sufficient period of time to allow the active to perform; they must not irritate the skin; and, they must be perceived by the patient as pharmaceutically elegant or the patient will simply not use them. By "pharmaceutically elegant", as those skilled in the art know, one means the feel to the patient is good. It must not be too watery or too greasy. Some say it relates to the creaminess or lubricity properties as well.

There is a continual need for improvements in topical carrier systems, particularly for those that are lipophilic in nature, most of which are perceived by consumers as too waxy or greasy when smeared on the skin.

As a result of the unique properties of the cream/ointments of the present invention, the preparation can be dosed effectively and conveniently from a squeeze-type dispenser, which is a desirable objective.

Accordingly, it is a primary object of the present invention to prepare a topical application or pharmaceutical composition which is of wide-spread applicability (i.e. useful with many drug actives) and which is at the same time perceived by the patient/user as pharmaceutically elegant.

Another objective of the present invention is to achieve the primary objective with a composition especially adapted for lipophilic bases and which can provide effective delivery in squeeze tube formats.

An even further objective is to achieve each of the above objectives in a cost effective manner so that the price can be maintained at reasonable levels, without the need for using expensive cosmetic carrier systems to achieve elegance.

A yet further objective is to provide a method of preparation of a topical ointment that achieves each of the above composition objectives or attributes.

The method and manner of achieving the above objectives will become apparent from the detailed description of the invention which follows.

SUMMARY OF THE INVENTION

A topical ointment pharmaceutical composition that uses a lipophilic base, a pharmaceutical active and, dispersed in the base, from about 1% to about 50% by weight of the total composition of hydrogenated non-melted castor oil in powder form. The result of using hydrogenated non-melted castor oil in powder form is a surprising pharmaceutical elegance perceived to be smoother in texture and more spreadable than can ointment mad e by melting the hydrogenated castor oil.

DETAILED DESCRIPTION OF A PREFERRED EMBODIMENT

For describing the compositions certain definitional terms are appropriate. "Pharmaceutically elegant" has been previously defined. The "pharmaceutical composition" as used throughout the present specification and the accompanying claims is to be understood as defining compositions of which the individual components or ingredients are themselves pharmaceutically acceptable, e.g. that is they are topically acceptable. Put another way, they are non-irritants, and they are either FDA approved or on the GRAS safe list. The term "topically active pharmaceutical" is intended to be non-limiting and includes those pharmaceutical active agents that are commonly applied topically such as waterproofing agents, skin barrier/skin protectant agents, skin conditioning agents, solvents, bio-adhesives, acne actives, analgesics, anesthetics, anorectals, antihistamines, anti-inflammatory agents, antibiotics, antifungals, antivirals, antimicrobials, scabicides, pediculicides, antineoplastics, antiperspirants, antipruritics, antisporadics, antiseborrheics, biologically active proteins and peptides, burn actives, cauterizing agents, depigment agents, diaper rash agents, enzymes, hair growth actives, kerotolytics, canker sore actives, cold sore actives, dental actives, saliva actives, photosensitizing actives, steroids, sunburn actives, sunscreens, wart actives, wound dressings and retinol, retinoic acid and retinoic acid derivatives. It is understood that this list is by way of example and not a limitation with respect to the active.

In the present compositions, there are three essential ingredients. The first is a lipophilic base normally selected from the group of vegetable oils, fatty acids, glycerides, or combinations thereof, including reaction combinations thereof. Thus, for example, fatty acid esters and fatty alcohols are included. The term "fatty" refers to higher carbon, generally $C_8$ to $C_{22}$. Suitable vegetable oils can include for example sunflower oil, safflower oil, castor oil, rapeseed oil, corn oil, Balsam Peru oil and soybean oil. Suitable fatty acids are generally $C_8$ to $C_{22}$ mono-and dicarboxylic fatty acids. They can include for example, stearic acid, oleic acid, myristic acid etc. Suitable fatty acid esters can include diisopropyl adipate, diisopropyl sebacate, diethyl sebacate, middle-length fatty acid triglycerides, middle-length acid propylene glycols, isopropyl myristate, and the like. Fatty alcohols can include cetanols, stearyl alcohol, cetostearyl alcohol, oleyl alcohol, behenyl alcohol, and the like.

The amount of the lipophilic base used is from about 20% to about 99% by weight of the total composition.

The second essential ingredient is the topically active pharmaceutical or in other words, the drug active. Suitable drug active categories have been previously listed. Generally the drug actives are present in amounts of from about 0.01% to about 10% by weight of the total composition.

The third essential ingredient and the one on which the discovery of the new invention is premised is, from about 1% by weight to about 50% by weight of the total pharmaceutical composition of hydrogenated, non-melted castor oil in powder form dispersed throughout the topical ointment. This changes dramatically the characteristics of the ointment. In particular, the ointment is smoother, more spreadable, perceived as less greasy or waxy in feel and functions effectively when dose dispensed from a squeeze tube. It does not happen if this is either not used or melted.

Critical to the invention, therefore, is that the hydrogenated castor oil powder be in a non-melted form. If it has been melted, it will not achieve the desired creaminess and lubricity of the present invention. Hydrogenated castor oil is itself known and can be obtained from a variety of sources, for example Henkel. Henkel has it available under the trademark CUTINA® HR NF and describes it as a slightly yellow fine free-flowing powder. It has an acid value of less than 3, a saponification value of 180, an iodine value of 5.0 and a hydroxy value of 160 with a melting range of 85° C. to 88° C. For further technical data and properties and application uses, see the technical data sheet of Henkel dated July 1999, a copy of which is being provided with the Information Disclosure Statement herein.

As earlier mentioned, the manner of preparation of the composition is equally important. It must be below the melt temperature of the hydrogenated castor oil and it must be prepared by dispersing under high shear mixing. Unexpectedly, when this occurs a matrix is formed in the lipophilic lipid base resulting in a semi-solid structure that is smoother, and more spreadable than a compound formulation made by simply melting hydrogenated castor oil into a lipid such as is conventional with, for example, lipstick. There are several advantages to a low temperature process. Exposures to high temperatures, which can degrade some ingredients such as active pharmaceutical ingredients or preservatives, can be avoided in a low temperature process. Temperature sensitive ingredients can be incorporated into the product at low temperatures prior to the formation of the semisolid structure. Exposing vegetable oils to high temperatures, especially unsaturated oils, can accelerate degradation and oxidation reactions resulting in the need for addition of antioxidants. Heating and cooling utility costs can be saved with a low temperature process. Manufacturing process times can be reduced with a low temperature process. The high shear mixing is achievable in a variety of mixing apparatus but one that is especially suitable is a high speed dispersator-type mixer. Another that is suitable is a rotor/stator-type emulsifier mixer. Yet a further one that provides satisfactory results is a high pressure-type emulsifier/mixer. By high shear mixing, it is meant that mixing occurs under high power per unit mass through rotating high shear forces. It is intended to distinguish this from more conventional formulary mixing apparatus such as planetary or anchor mixers.

The composition may contain other ingredients as well. These include viscosity modifiers, solvents, surfactants, preservatives, fragrances, waterproofing and skin barrier agents, etc.

Suitable viscosity adjusting agents (i.e., thickening and thinning agents) for use in the formulations of the present invention include, but are not limited to silica, microcrystalline wax, beeswax, paraffin, and cetyl palmitate. In addition, appropriate combinations or mixtures of these viscosity adjusters may be utilized according to the present invention.

Suitable solvents for use in the formulations of the present invention include, but are not limited to, water, ethanol, butylene glycol, dimethyl isosorbide, propylene glycol, isopropyl alcohol, glycerin, ethoxydiglycol, Pharmasolve, Carbowax 200, Carbowax 400, Carbowax 600, and Carbowax 800. In addition, combinations or mixtures of these solvents may be used according to the present invention.

Suitable surfactants for use in the formulations of the present invention include, but are not limited to nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Appropriate combinations or mixtures of such surfactants may also be used accordingly to the present invention.

Suitable preservatives for use in the formulations of the present invention include, but are not limited to, antimicrobials such as Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, and formaldehyde, as well as physical stabilizers and antioxidants such as alphatocopherol (vitamin E), sodium ascorbate/ascorbic acid, ascorbyl palmitate and propyl gallate. In addition, combinations or mixtures of these preservatives may also be used in the formulations of the present invention.

Suitable moisturizers for use in the formulations of the present invention include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations of the present invention include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200–100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors, such as FD&C Red No. 40 and FD&C Yellow No. 5, may be used in the formulations of the present invention. Other examples of fragrances and colors suitable for use in topical products are known in the art.

Suitable waterproofing and skin barrier agents include but are not limited to aluminum/magnesium hydroxide stearate, calcium stearate, aluminum stearate, magnesium stearate, dimethicone, and PTFE compounds.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, and protectants. Examples of each of these ingredients, as well as examples of other suitable ingredients in topical product formulations, may be found in publications by The Cosmetic, Toiletry, and Fragrance Association (CTFA). See, e.g., *CTFA Cosmetic Ingredient Handbook*, $2^{nd}$ edition, eds. John A. Wenninger and G. N. McEwen, Jr. (CTFA, 1992).

Examples of various formulations taking advantage of the hydrogenated castor oil in non-melted form system of the present invention, and each having various rheological properties, are set forth below.

The following example is offered to further illustrate but not limit the invention. An anhydrous lipophilic pharmaceutical topical ointment comprised of a lipid and powdered hydrogenated castor oil (such as CUTINA® HR from the Henkel Corporation) that can be used as a vehicle for pharmaceutical actives was prepared.

The ointment was prepared by dispersing the powdered hydrogenated castor oil into the lipid at a temperature less than the melting point of the hydrogenated castor oil in particular at below 42° C. The dispersion of the fine particles of the hydrogenated castor oil forms a semisolid structure in the lipid when subjected to the high shear mix.

The texture of this ointment is smoother and more spreadable than that of an ointment made by melting hydrogenated castor oil into the lipid, which obtains its structure by the crystallization of the hydrogenated castor oil upon cooling.

The lipid used was a vegetable oil (castor oil) but could be a fatty acid, a glyceride, an ester or mixtures thereof.

EXAMPLE 1

|  | % w/w |
|---|---|
| Castor Oil | 90.0 |
| Hydrogenated Castor Oil (CUTINA ® HR) | 10.0 |

The hydrogenated castor oil was added to the castor oil while mixing with a high shear mixer and mixed until a semisolid was formed. It was noted and tested for elegance. In particular, a tactile and visual examination of the preparation revealed a smooth, creamy texture that was spreadable on the skin.

EXAMPLE 2

A wound debrider of the following formula was prepared.

|  | % w/w |
|---|---|
| Castor Oil | 68.8 |
| Hydrogenated Castor Oil | 10.0 |
| Balsam Peru Oil | 8.70 |
| Aluminum/Magnesium Hydroxide Stearate | 2.00 |
| Trypsin | 0.018 |
| Safflower Oil | q.s. ad 100% |

In preparation of the composition of Example 2, which is an enzymatic wound debrider, the aluminum/magnesium hydroxide stearate was dispersed in the castor oil. Thereafter the hydrogenated castor oil was added while mixing with a high shear mixer. In particular a Lee Tri-Mix Turbo-Shear Mixer was used. Mixing was continued until a semi-solid formed. The remaining ingredients were then blended to the semi-solid until homogeneous mixing appeared.

From the above data, it can be seen that the invention accomplishes all of its objectives.

What is claimed is:

1. A topical ointment pharmaceutical composition, comprising:
    a lipophilic base selected from the group consisting of vegetable oils, fatty acids, glycerides, and combinations thereof;
    a small but pharmaceutically-effective amount of topically active pharmaceutical;
    from about 1% by weight to 50% by weight of the total pharmaceutical composition of hydrogenated, non-melted castor oil in powder form dispersed in the topical ointment pharmaceutical composition.

2. The topical ointment pharmaceutical composition of claim 1 wherein the amount of hydrogenated, non-melted castor oil in powder form dispersed in the topical ointment composition is from about 1% by weight of the total composition to about 25% by weight of the total composition.

3. The topical ointment pharmaceutical composition of claim 1 wherein the amount of hydrogenated, non-melted castor oil in powder form dispersed in the topical ointment composition is from about 1% by weight of the total composition to about 15% by weight of the total composition.

4. The topical ointment pharmaceutical composition of claim 1 wherein the lipophilic base is selected from the group consisting of sunflower oil, safflower oil, castor oil, rape seed oil, corn oil, Balsam Peru oil, soybean oil, fatty acids, fatty acid esters, higher alcohols and glycerides.

5. The composition of claim 1 wherein the topically active pharmaceutical is selected from the group consisting of acne actives, analgesics, anesthetics, anorectals, antihistamines, anti-inflammatory agents, antibiotics, antifungals, antivirals, antimicrobials, scabicides, pediculicides, antineoplastics, antiperspirants, antipruritics, antisporadics, antiseborrheics, biologically active proteins and peptides, burn actives, cauterizing agents, depigmenting agents, diaper rash agents, enzymes, hair growth actives, kerotolytics, canker sore actives, cold sore actives, dental actives, saliva actives, photosensitizing actives, skin protectant/barrier agents, steroids, sunburn actives, sunscreens, wart actives, wound dressing products and retinol, retinoic acid and retinoic acid derivatives.

6. The method of making a topically ointment pharmaceutical composition comprising:
    admixing a lipophilic base selected from the group consisting of vegetable oils, fatty acids, glycerides and combinations thereof, with a small but pharmaceutically effective amount of a topically active pharmaceutical and from about 1% to 50% by weight of the total composition being hydrogenated non-melted castor oil in powder form;
    said mixing occurring in a high shear mixer at a temperature below the melt temperature of the hydrogenated non-melted castor oil in powder form.

* * * * *